(12) United States Patent
Ansari et al.

(10) Patent No.: US 11,370,729 B2
(45) Date of Patent: Jun. 28, 2022

(54) PROGRAMMABLE LOGIC CONTROLLER IN DEHYDROGENATION PROCESS

(71) Applicant: SABIC Global Technologies B.V., Bergen op Zoom (NL)

(72) Inventors: Mohammed Bismillah Ansari, Riyadh (SA); Vijay Dinkar Bodas, Riyadh (SA); Guillermo Leal, Riyadh (SA); Sultan Al-Otaibe, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 204 days.

(21) Appl. No.: 16/604,215

(22) PCT Filed: May 1, 2018

(86) PCT No.: PCT/IB2018/053012
§ 371 (c)(1),
(2) Date: Oct. 10, 2019

(87) PCT Pub. No.: WO2018/203233
PCT Pub. Date: Nov. 8, 2018

(65) Prior Publication Data
US 2020/0031739 A1 Jan. 30, 2020

Related U.S. Application Data
(60) Provisional application No. 62/500,994, filed on May 3, 2017.

(51) Int. Cl.
*C07C 5/333* (2006.01)
*B01J 8/00* (2006.01)
(Continued)

(52) U.S. Cl.
CPC .............. *C07C 5/333* (2013.01); *B01J 8/001* (2013.01); *B01J 8/0278* (2013.01); *B01J 23/26* (2013.01);
(Continued)

(58) Field of Classification Search
CPC ......... C07C 5/333; B01J 8/001; B01J 8/0278; B01J 23/26; B01J 23/626; B01J 32/02;
(Continued)

(56) References Cited

U.S. PATENT DOCUMENTS

| 2,831,041 A | * | 4/1958 | Sieg | ........................ C07C 11/10 585/624 |
| 4,581,339 A | | 4/1986 | Bhatt et al. | ...................... 502/38 |

(Continued)

FOREIGN PATENT DOCUMENTS

| FR | 74186 E | 11/1960 |
| GB | 823626 A | 11/1959 |

(Continued)

OTHER PUBLICATIONS

International Search Report and Written Opinion for PCT/IB2018/053012 dated Jul. 26, 2018, 12 pages.

*Primary Examiner* — Thuan D Dang
(74) *Attorney, Agent, or Firm* — Norton Rose Fulbright US LLP (57) ABSTRACT

Systems and methods of dehydrogenating a hydrocarbon in a fixed bed dehydrogenation unit. A method for dehydrogenating a hydrocarbon is applied to a fixed bed reactor. The hydrocarbon flows to a fixed bed reactor to be dehydrogenated in presence of a catalyst in the fixed bed reactor. The catalyst in the fixed bed reactor is then regenerated. The period for dehydrogenation, the period for catalyst regeneration and the period for total slack time are controlled such that total slack time is less than both half of the period for (Continued)

dehydrogenation and half of the period for regeneration. One of the advantages of the process comes from optimization of the slack time, thereby increasing the catalyst utilization rate and number of reactors concurrently online.

19 Claims, 4 Drawing Sheets

(51) Int. Cl.
  *B01J 8/02* (2006.01)
  *B01J 23/26* (2006.01)
  *B01J 23/62* (2006.01)
  *B01J 38/02* (2006.01)

(52) U.S. Cl.
  CPC ............ *B01J 23/626* (2013.01); *B01J 38/02* (2013.01); *B01J 2208/00725* (2013.01)

(58) Field of Classification Search
  CPC ......... B01J 2208/00725; B01J 19/0006; Y02P 20/52; Y02P 20/584
  See application file for complete search history.

(56) References Cited

U.S. PATENT DOCUMENTS

| | | |
|---|---|---|
| 4,789,528 A | 12/1988 | Owen et al. ................. 422/619 |
| 2004/0015012 A1 | 1/2004 | Hammon et al. ............ 562/532 |
| 2004/0087825 A1 | 5/2004 | Urbancic et al. ............ 585/660 |
| 2015/0375209 A1 | 12/2015 | Fan et al. |
| 2016/0168052 A1 | 6/2016 | Schwint et al. |

FOREIGN PATENT DOCUMENTS

| | | |
|---|---|---|
| WO | WO2014035888 A1 | 3/2014 |
| WO | WO2004092908 A2 | 6/2014 |

\* cited by examiner

PROGRAMMABLE LOGIC CONTROLLER IN DEHYDROGENATION PROCESS

CROSS REFERENCE TO RELATED APPLICATIONS

This application is a national phase application under 35 U.S.C. § 371 of International Application No. PCT/IB2018/053012 filed May 1, 2018, which claims priority to U.S. Provisional Patent Application No. 62/500,994 filed May 3, 2017. The entire contents of each of the above-referenced disclosures is specifically incorporated by reference herein without disclaimer.

FIELD OF INVENTION

The present invention generally relates to process control for chemical production units. More specifically, the present invention relates to programmable logic controllers for fixed bed dehydrogenation units.

BACKGROUND OF THE INVENTION

Fixed bed dehydrogenation units are used for on-purpose production of olefins and/or alkynes from alkanes and/or olefins. Generally, a fixed bed dehydrogenation unit comprises three or more parallel fixed bed reactors and a catalyst regeneration system. When the fixed bed dehydrogenation unit is in operation, one or more reactors are on line (in dehydrogenation mode), and one or more fixed bed reactors are in regeneration mode. Additional fixed bed reactors might be in standby mode. A fixed bed reactor in dehydrogenation mode first dehydrogenates the hydrocarbon feed for a period of time. Then, the fixed bed reactor is purged with steam. In a subsequent regeneration mode, heated air is blown through to decoke the catalyst disposed in the fixed bed reactor. The reactor is in turn evacuated and the catalyst in the reactor undergoes reduction. After catalyst reduction, the reactor is placed back on line for dehydrogenation reactions. The same sequence is repeated automatically for each fixed bed reactor using a programmable logic controller (PLC) to ensure continuous production of the entire dehydrogenation unit.

Commercial programmable logic controllers often employ simplified algorithms to program the fixed bed dehydrogenation units with an inflexible and conservative approach. These algorithms do not factor in modifications in process, catalyst conditions, or correlations between reaction duration and catalyst activity profiles. Often, reactors proceed to the regeneration process before the catalyst is fully deactivated. Thus, the catalyst in these fixed bed dehydrogenation units are under-utilized, resulting in low efficiency of the catalyst, thereby increasing operating costs. Therefore, a process controller that causes the full utilization of the catalyst and reactors in a fixed bed dehydrogenation unit is desired.

BRIEF SUMMARY OF THE INVENTION

A method has been discovered for efficiently dehydrogenating a hydrocarbon in a fixed bed reactor via optimized process control. By optimizing the dehydrogenation time and regeneration time for the fixed bed dehydrogenation reactor, the utilization rate of the fixed bed dehydrogenation reactor is increased, thereby improving the efficiency of the fixed bed reactor and reducing operating costs without substantial capital expenditure.

Embodiments of the invention include a method of dehydrogenating a hydrocarbon. The method may comprise flowing the hydrocarbon to a fixed bed reactor and dehydrogenating the hydrocarbon in presence of a catalyst in the fixed bed reactor for period X, where the catalyst life expectancy is L. The method may further include regenerating, after period X, the catalyst for period Y. There may be a period $Z_1$ between the dehydrogenating step and the regenerating step. The method may further include repeating the dehydrogenating, after period Y. There may be a period $Z_2$ between the regenerating and the repeating. A cycle of operating the fixed bed reactor is equal to X+Y+Z, where Z is a total period of the cycle, in which neither the dehydrogenating step nor regenerating step is being carried out. The method may further include controlling the length of period X, the length of period Y, and the length of period Z by a controller such that Z<X/2 and Z<Y/2.

Embodiments of the invention include a method of dehydrogenating a hydrocarbon in a fixed bed dehydrogenation unit that comprises one or more fixed bed dehydrogenation reactors. The method may comprise flowing the hydrocarbon to one or more of the fixed bed reactors of the fixed bed dehydrogenation unit and dehydrogenating the hydrocarbon in presence of a catalyst in the one or more fixed bed reactors for period X, where the catalyst life expectancy is L. The method may further include regenerating, after period X, the catalyst for period Y. There may be a period $Z_1$ between the dehydrogenating and the regenerating. The method may further include repeating the dehydrogenating, after period Y. There may be a period $Z_2$ between the regenerating and the repeating. A cycle of operating each of the fixed bed reactor is equal to X+Y+Z, where Z is a total period of the cycle in which neither the dehydrogenating step nor regenerating step is being carried out. The method may further include controlling the length of period X, the length of period Y, and the length of period Z of the one or more fixed bed dehydrogenation reactors by a controller such that Z<X/2 and Z<Y/2.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

In the context of the present invention at least seventeen embodiments are now described. Embodiment 1 relates to a method of dehydrogenating a hydrocarbon. The method of embodiment 1 includes the steps of (1) flowing the hydrocarbon to a fixed bed reactor; (2) dehydrogenating the hydrocarbon in presence of a catalyst in the fixed bed reactor for period X, wherein the catalyst has life expectancy L; (3) regenerating, after period X, the catalyst for period Y, wherein $Z_1$ is a period between (2) and (3), if any, (4) repeating (2), after period Y, wherein $Z_2$ is a period between (3) and (4), if any, wherein $Z_1 > 0$ and/or $Z_2 > 0$ and $Z = Z_1 + Z_2$, wherein a cycle of operating the fixed bed reactor is equal to X+Y+Z, wherein Z is a total period of the cycle in which neither (2) nor (3) is being carried out; and (5) controlling the length of period X, the length of period Y, and the length of period Z, by a controller, such that $Z < X/2$ and $Z < Y/2$. Embodiment 2 is the method of embodiment 1, wherein the fixed bed reactor is disposed in a fixed bed dehydrogenation unit, the fixed bed dehydrogenation unit includes one or more fixed bed reactors. Embodiment 3 is the method of any of embodiments 1 to 2, wherein the hydrocarbon is selected from the group consisting of on propane, isobutane, pentane, isopentane, n-butane, and combinations thereof. Embodiment 4 is the method of any of embodiments 1 to 3, wherein period X is in a range of 7 to 18 minutes, Y is in a range of 7 to 18 minutes, and Z is in arrange of 3.5 to 8.7 minutes. Embodiment 5 is the method of any of embodiments 1 to 4, wherein period X, period Y and total slack time Z in controlling step (5) are determined by a mathematical model based on one or more correlations between (a) X, Y and/or Z and (b) one or more operating parameters and/or factors of the fixed bed reactor. Embodiment 6 is the method of embodiment 5, wherein the one or more operating parameters and/or factors of the fixed bed reactor are selected from the group consisting of days on stream (DOS)(days on line), changes in process, number of fixed bed reactors in the dehydrogenation unit, catalyst conditions, and combinations thereof. Embodiment 7 is the method of embodiment 6, wherein the changes in process include changing the hydrocarbon flowing to the fixed bed reactor, and wherein the hydrocarbon is one or more of propane, isobutane, pentane, isopentane, or n-butane. Embodiment 8 is the method of embodiment 6, wherein the catalyst conditions are selected from the group consisting of a reaction temperature, a reaction pressure, weight hourly space velocity, type of catalysts, and combinations thereof. Embodiment 9 is the method of embodiment 8, wherein the reaction temperature is in a range of 540° C. to 750° C. Embodiment 10 is the method of embodiment 8, wherein the reaction pressure is in a range of 0.2 bar to 1.2 bar. Embodiment 11 is the method of embodiment 8, wherein the weight hourly space velocity is in a range of 1 to 1.6. Embodiment 12 is the method of any of embodiments 5 and 6, wherein the correlations include a linear correlation between a ratio of X to Y and days on stream (days on line). Embodiment 13 is the method of embodiment 12, wherein a total length of period X and period Y is constant over cycles throughout life expectancy L. Embodiment 14 is the method of any of embodiments 12 and 13, wherein the linear correlation is determined by linear regression on operating data of the fixed bed dehydrogenation unit. Embodiment 15 is the method of any of embodiments 5 and 6, wherein the correlations include a polynomial correlation between (a) X, Y, Z and/or a ratio of X to Y and (b) the one or more operating parameters and/or factors of the fixed bed reactor, and wherein the polynomial correlation is obtained using polynomial regression based on operating data of the fixed bed dehydrogenation unit. Embodiment 16 is the method of any of embodiments 5 and 6, wherein the correlations between (a) X, Y and/or Z and (b) the one or more operating parameters and/or factors are obtained by multivariate multiple regression. Embodiment 17 is a non-transitory computer-readable storage medium storing instructions that, when executed by one or more processors, cause the one or more processors to perform the method of any of embodiments 1 to 16.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for dehydrogenating a hydrocarbon in a fixed bed dehydrogenation unit comprising one or more parallel fixed bed reactors. By implementing the method in the dehydrogenation unit, the utilization rate of the fixed bed reactors increases, thereby improving the efficiency of the fixed bed dehydrogenation unit and reducing production cost without substantial capital expenditure.

Figure 1:
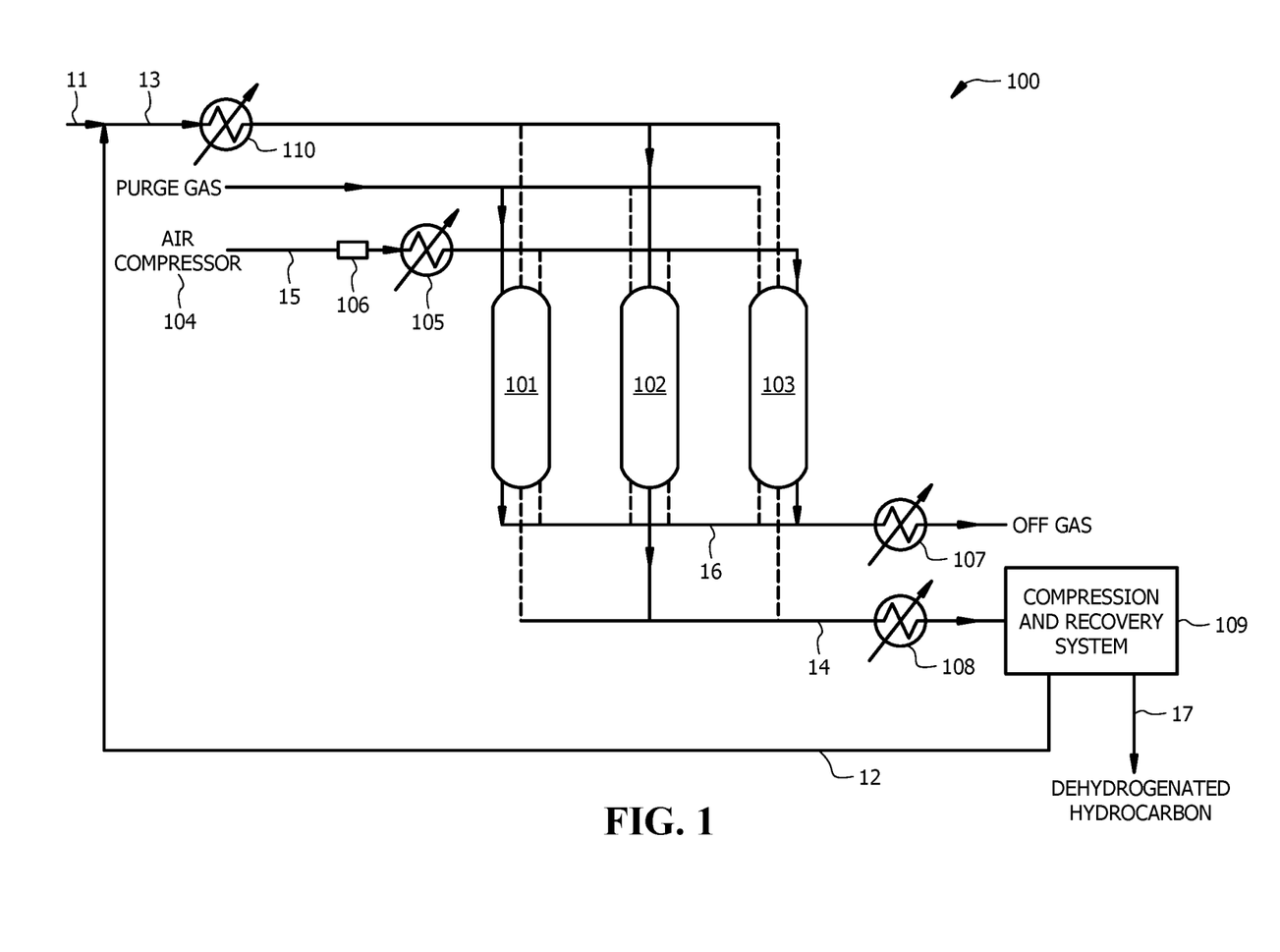
FIG. 1 shows a schematic diagram for a fixed bed dehydrogenation unit, according to embodiments of the invention.

With reference to FIG. 1, a process schematic diagram is shown as fixed bed dehydrogenation unit 100. As shown in FIG. 1, fixed bed dehydrogenation unit 100 may include fixed bed reactor 101 in purge mode, fixed bed reactor 102 in dehydrogenation mode, and fixed bed reactor 103 in regeneration mode. Each of the fixed bed reactors comprises a catalyst bed. The catalyst may include Cr/Al (chromium oxide over alumina), Sn—Pt/Al (tin-platinum over alumina), or combinations thereof. The inlet of fixed bed reactor 102 in dehydrogenation mode may be connected to heater 110 that is configured to heat a hydrocarbon feed to a reaction temperature, and the outlet of fixed bed reactor 102 in dehydrogenation mode may be connected to heat exchanger 108 to cool down the effluent from fixed bed reactor 102 in dehydrogenation mode. Fixed bed dehydrogenation unit 100 may further include a regeneration air system comprising air compressor 104 configured to blow air into fixed bed reactor 103 in regeneration mode, regeneration air heater 105 configured to heat the air from air compressor 104, fuel injector 106 configured to inject fuel gas into fixed bed reactor 103 in regeneration mode, and heat exchanger 107 configured to cool down the effluents from fixed bed reactor 103 in regeneration mode and fixed bed reactor 101 in purge mode. Fuel injector 106 may be disposed between air compressor 104 and air heater 105. Heat exchanger 107 may be connected to the outlets of fixed bed reactor 103 in regeneration mode. The fixed bed dehydrogenation unit 100 may further include a compression and recovery system 109 to recover and purify a dehydrogenated hydrocarbon obtained from fixed bed reactor 102 on line (in dehydrogenation mode).

Figure 2:
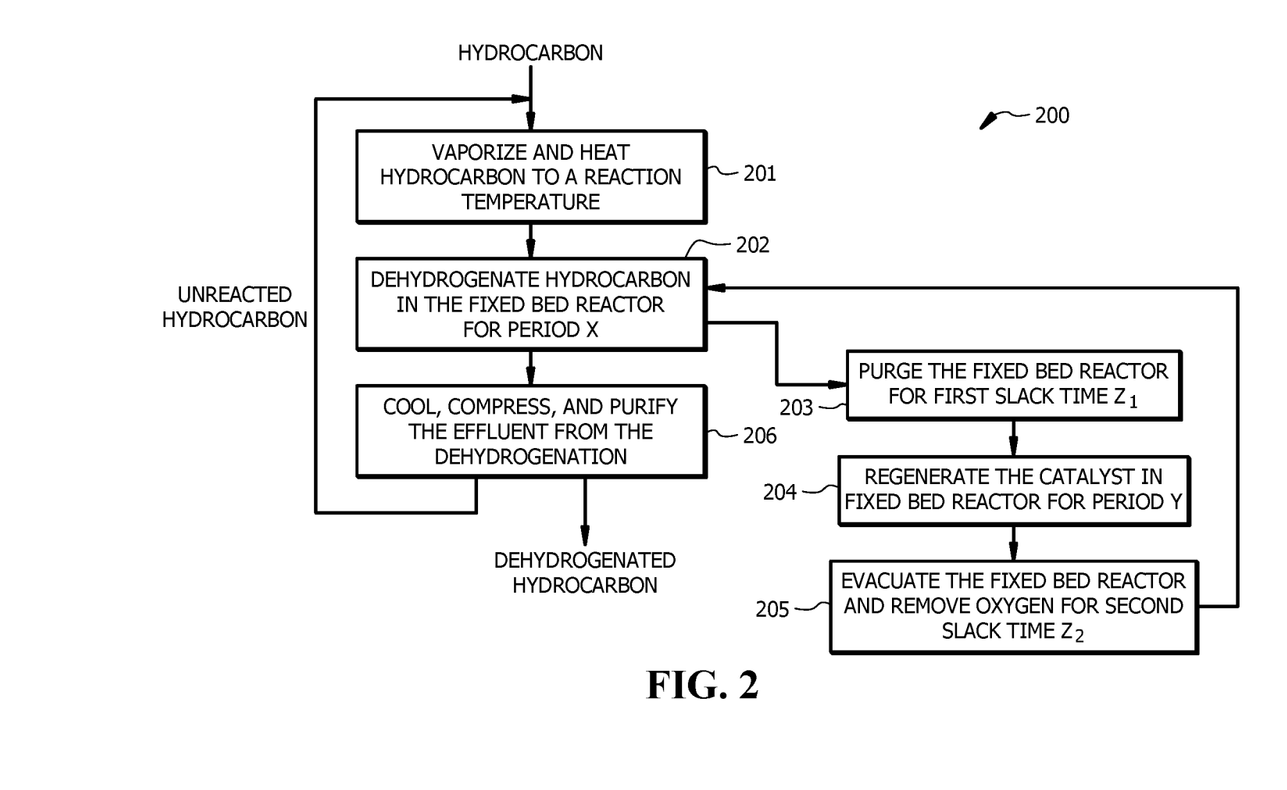
FIG. 2 shows a flowchart of a method for dehydrogenating a hydrocarbon, according to embodiments of the invention.

FIG. 2 shows method 200 for dehydrogenating a hydrocarbon. Method 200 may be implemented by fixed bed dehydrogenation unit 100 as shown in FIG. 1. The process may start with hydrocarbon feed stream 11 combined with recycled hydrocarbon stream 12 from compression and recovery system 109 to form combined hydrocarbon stream 13. The hydrocarbon may include propane, isobutane, pentane, isopentane, n-butane, or combinations thereof. The product (dehydrogenated hydrocarbon) of the fixed bed dehydrogenation unit may comprise propylene, isobutylene, pentene, isoprene, butadiene, or combinations thereof. The dehydrogenation reactions in method 200, carried out by dehydrogenation unit 100, may include reactions (i) and/or (ii) as follows, where "n" in reactions (i) and (ii) is the number of carbon atoms in a hydrocarbon molecule, and "n" is less than 5:

$$C_nH_{2n+2} \leftrightarrow C_nH_{2n} + H_2 \quad \text{(i), and/or}$$

$$C_nH_{2n} \leftrightarrow C_nH_{2n-2} + H_2 \quad \text{(ii)}$$

Block 201 of FIG. 2 shows that combined hydrocarbon stream 13 from hydrocarbon feed stream 11 and recycled hydrocarbon stream 12 may be vaporized and heated to a reaction temperature by heater 110. The reaction temperature may be 540° C. to 750° C. Further, combined hydrocarbon stream 13 at the reaction temperature may flow in fixed bed reactor 102, which is in dehydrogenation mode (on line). As shown in block 202, hydrocarbons in combined hydrocarbon stream 13 may be dehydrogenated. Effluent stream 14 from fixed bed reactor 102 in dehydrogenation mode may be cooled by heat exchanger 108 to generate steam. After dehydrogenation period X, fixed bed reactor 102 in dehydrogenation mode may be purged with steam for a period of first slacking time $Z_1$, as shown in block 203, to remove residual hydrocarbons from the catalyst. Therefore, fixed bed reactor 102 in dehydrogenation mode enters purge mode for first slack time $Z_1$.

Subsequently, as shown in block 204, fixed bed reactor 101 in purge mode may be regenerated for regeneration period Y, thereby fixed bed reactor 101 in purge mode enters regeneration mode. In block 204, air from air compressor 104 via stream 15 may be heated by air heater 105. Heated air passes through fixed bed reactor 103 in regeneration mode to decoke the catalyst and restore the catalyst to its initial on line condition. A fuel may be injected and combusted in fixed bed reactor 103 in regeneration mode.

After regeneration period Y, fixed bed reactor 103 in regeneration mode may be evacuated and a fuel gas may be injected into the reactor to remove oxygen adsorbed in the bed for second slack time $Z_2$, as shown in block 205. Fixed bed reactor 103 in regeneration mode is ready to enter dehydrogenation mode (on line) after second slack time $Z_2$. Stream 16 leaving fixed bed reactor 103 in regeneration mode may be used for generating steam via heat exchanger 107. Block 206 shows that effluent stream 14 from fixed bed reactor 102 in dehydrogenation mode may be cooled, recovered, and purified through recovery system 109. Purified dehydrogenated hydrocarbon may flow in stream 17. Recovered unreacted hydrocarbon may be recycled back to combined hydrocarbon stream 13 via recycled hydrocarbon stream 12.

Figure 3:
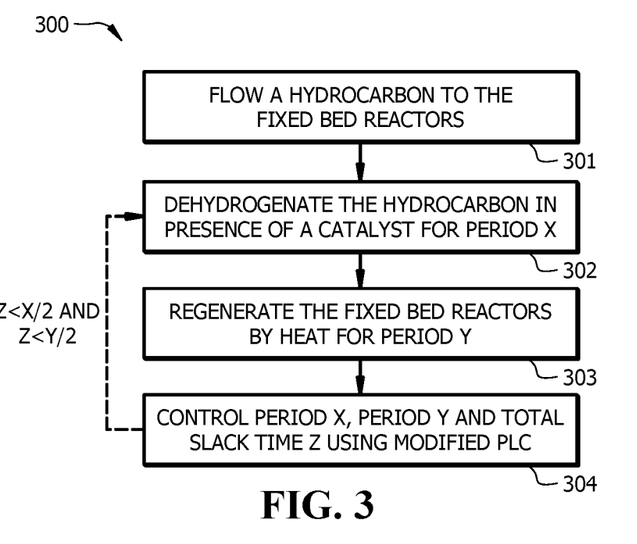
FIG. 3 shows a schematic flowchart for a method of dehydrogenating a hydrocarbon using the modified programmable logic controller, according to embodiments of the invention.

As shown in FIG. 3, embodiments of the invention include method 300 for dehydrogenating a hydrocarbon in a fixed bed dehydrogenation unit which comprises one or more fixed bed reactors. Block 301 shows that method 300 may comprise flowing the hydrocarbon to the one or more fixed bed reactors. The hydrocarbon may be dehydrogenated in the presence of a catalyst in one or more fixed bed reactors for period X as shown in block 302. In embodiments of the invention, period X may be in a range of 7 to 18 minutes, and all ranges and values there between including 7 to 8 minutes, 8 to 9 minutes, 9 to 10 minutes, 10 to 11 minutes, 11 to 12 minutes, 12 to 13 minutes, 13 to 14 minutes, 14 to 15 minutes, 15 to 16 minutes, 16 to 17 minutes, or 17 to 18 minutes. The catalyst in the fixed bed reactors of fixed bed dehydrogenation unit 100 may have life expectancy L. In embodiments of the invention, life expectancy L of the catalyst may be 0 to 36 months. After block 302, block 303 shows that the catalyst in the one or more fixed bed reactors may be regenerated for period Y. In embodiments of the invention, period Y may be 7 to 18 minutes and all ranges and values there between including 7 to 8 minutes, 8 to 9 minutes, 9 to 10 minutes, 10 to 11 minutes, 11 to 12 minutes, 12 to 13 minutes, 13 to 14 minutes, 14 to 15 minutes, 15 to 16 minutes, 16 to 17 minutes, or 17 to 18 minutes.

Block 302 to block 303 may be repeated after block 303. In embodiments of the invention, first slack time $Z_1$ may be a slack time between block 302 and block 303. First slack time $Z_1$ may include time for purging the one or more fixed bed reactors after period X. Steam may be used to purge the fixed bed reactors after period X to strip residual hydrocarbon from the catalyst. Second slack time $Z_2$ may be a slack time between block 303 and repeated block 302. Second slack time $Z_2$ may include time to evacuate the one or more fixed bed reactors after catalyst regeneration, time for removing oxygen adsorbed on the catalyst via combustion of fuel gas, or combinations thereof. Total slack time Z may be a time period neither block 302 nor block 303 is performed in a fixed bed reactor during a cycle. In embodiments of the invention, total slack time may be a sum of first slack time $Z_1$ and second slack time $Z_2$. A cycle of operating the fixed bed reactor may be a sum of period X, period Y and total slack time Z. In embodiments of the invention, total slack time Z may be in a range of about 3.5 to 8.7 minutes, and all ranges and values there between, including 3.5 to 4.0 minutes, 4.0 to 4.5 minutes, 4.5 to 5.0 minutes, 5.0 to 5.5 minutes, 5.5 to 6.0 minutes, 6.0 to 6.5 minutes, 6.5 to 7.0 minutes, 7.0 to 7.5 minutes, 7.5 to 8.0 minutes, or 8.0 to 8.7 minutes.

As shown in block 304, method 300 for dehydrogenating a hydrocarbon in a fixed bed dehydrogenation unit may further include controlling the length of period X, the length of period Y and the length of total slack time Z by a programmable logic controller. The total slack time may be shorter than both X/2 and Y/2. In embodiments of the invention, period X, period Y and total slack time Z in the controlling may be determined by a mathematical model based on one or more correlations between (a) operating periods which include period X, period Y, first slack time $Z_1$, second slack time $Z_2$ and/or total slack time Z, and (b) one or more operating parameters and/or operating factors of the fixed bed reactor. The one or more operating parameters and/or factors of the fixed bed reactor may comprise days on stream (on line), changes in process, number of fixed bed reactors in the dehydrogenation unit, catalyst conditions, improper heat input, partial effect of lump formation, unexpected activity decay of catalyst, or combinations thereof.

According to embodiments of the invention, the changes in process may include change of the feed material, which may be one or more of propane, isobutene, isopentane, and/or n-butane. The catalyst conditions may include the type of catalyst (chromium oxide over alumina or tin-platinum over alumina) used in the reactors and the reaction conditions. In embodiments of the invention, the reaction conditions may include reaction temperature, reaction pressure and weight hourly space velocity (weight flowrate of the feed divided by the catalyst weight), or combinations thereof. The reaction temperature may be in a range of 540° C. to 750° C. and all ranges and values there between including ranges of 540° C. to 550° C., 550° C. to 560° C., 560° C. to 570° C., 570° C. to 580° C., 580° C. to 590° C., 590° C. to 600° C., 600° C. to 610° C., 610° C. to 620° C., 620° C. to 630° C., 630° C. to 640° C., 640° C. to 650° C., 650° C. to 660° C., 660° C. to 670° C., 670° C. to 680° C., 680° C. to 690° C., 690° C. to 700° C., 700° C. to 710° C., 710° C. to 720° C., 720° C. to 730° C., 730° C. to 740° C., or 740° C. to 750° C. The reaction pressure may be in a range of 0.2 to 1.2 bar and all ranges and values there between including 0.2 bar, 0.3 bar, 0.4 bar, 0.5 bar, 0.6 bar, 0.7 bar, 0.8 bar, 0.9 bar, 1.0 bar, 1.1 bar, or 1.2 bar. The weight hourly space velocity may be in a range of 1 to 1.6 and all ranges and values there between including 1, 1.1, 1.2, 1.3, 1.4, 1.5 or 1.6. In embodiments of the invention, the correlations may include a linear correlation between a ratio of X/Y and days on stream (on line) for the fixed bed reactor. The total length of period X and period Y may be constant. The linear correlation may be determined using linear regression on operating data of the fixed bed dehydrogenation unit.

Alternatively or additionally, the correlation between (a) period X, period Y, first slack time $Z_1$, second slack time $Z_2$ and/or total slack time Z and (b) one or more operating parameters and/or operating factors of the fixed bed reactor may further include a polynomial correlation determined via polynomial regression on operating data of the dehydrogenation unit, and/or other multivariate correlations via multivariate regression on the operating data of the dehydrogenation unit. In embodiments of the invention, block 302 to block 303 may be repeated after block 304.

Figure 4:
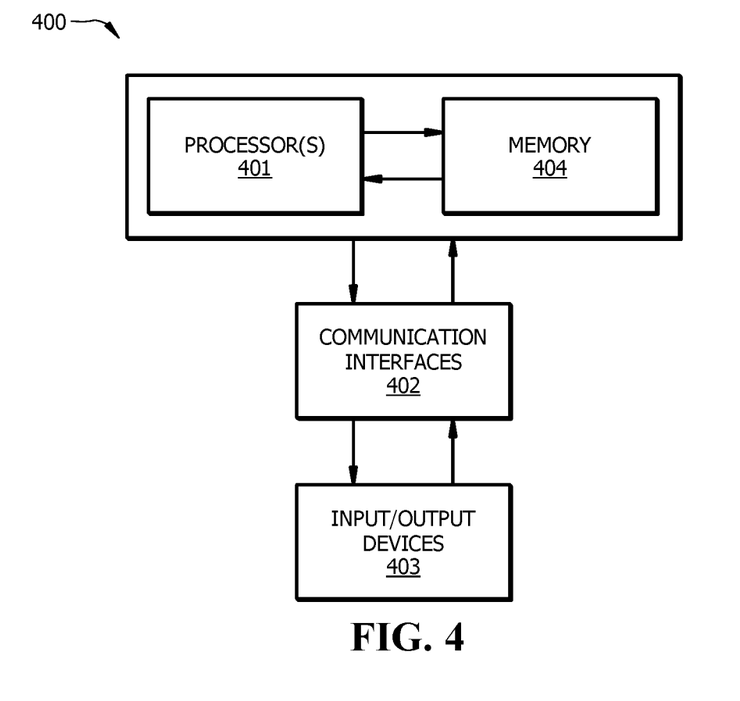
FIG. 4 shows a schematic diagram of a process control system, according to embodiments of the invention.

Embodiments of the invention provide a control system for controlling the process of dehydrogenating a hydrocarbon in a fixed bed dehydrogenation unit. As shown in FIG. 4, control system 400 may include one or more processors 401, one or more communication interfaces 402, one or more input/output devices 403, and memory 404. The memory 404 may include one or more random access memory (RAM) devices, read only memory (ROM) devices, one or more hard disk drives (HDDs), flash memory devices, solid state drives (SSDs), network attached storage (NAS) devices, other devices configured to store data in a persistent or non-persistent state, or a combination of different memory devices. In embodiments of the invention, memory 404 may comprise a non-transitory storage medium storing instructions that, when executed by one or more processors 401, cause one or more processors 401 to perform operations for analyzing, controlling, or both, dehydrogenating a hydrocarbon by one or more fixed bed reactors of a fixed bed dehydrogenation unit. In embodiments of the invention, the operations may include the block 301 to block 304 shown in FIG. 3 and all the processes of method 300.

Figure 5:
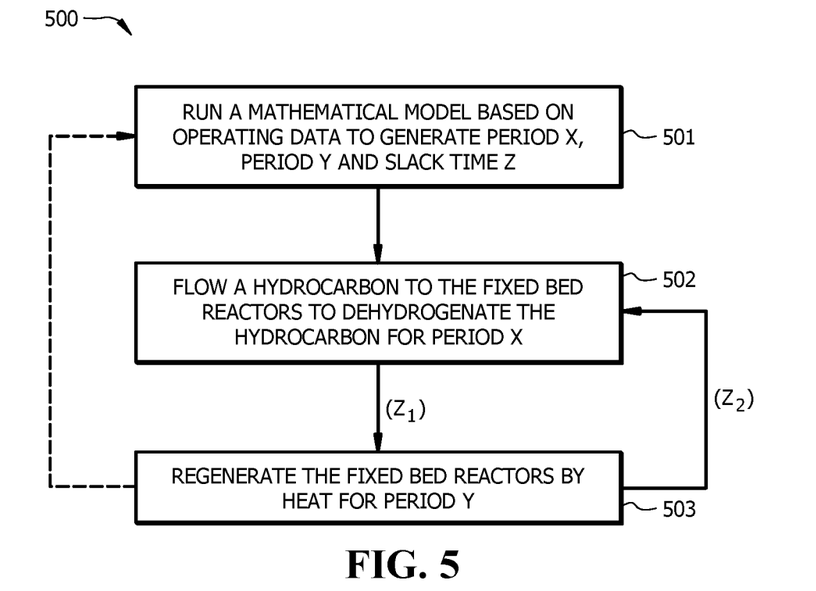
FIG. 5 shows a schematic flowchart for operations performed by a fixed bed dehydrogenation unit using a process control system, according to embodiments of the invention.

As shown in FIG. 5, in embodiments of the invention, block 501 shows that the operations may further include running a mathematical model, with input including operating parameters and/or operating factors of the one or more fixed bed reactors, to generate an output comprising dehydrogenation period X, regeneration period Y, total slack time Z, first slack time $Z_1$ and second slack time $Z_2$ for each fixed bed reactor, where total slack time Z is a sum of first slack time $Z_1$ and second slack time $Z_2$. The operations may further include flowing a hydrocarbon through two or more of the fixed bed reactors operating in parallel, as shown in block 502. In embodiments of the invention, the mathematical model may be run in tandem with other existing mathematical models. Block 503 shows catalyst in the fixed bed reactors may be regenerated after dehydrogenation period X, and first slack time $Z_1$. The operations may further include repeating block 502 after the regenerating period Y and second slack time $Z_2$. Additionally or alternatively, before repeating block 502, based on changes of operating parameters and/or operating factors, the mathematical model from block 501 may be run again to generate a second output including an updated dehydrogenation period X, an updated regeneration period Y, an updated total slack time Z, an updated first slack time $Z_1$, an updated second slack time $Z_2$, or combinations thereof.

Although embodiments of the present invention have been described with reference to blocks of FIGS. 2, 3 and 5, it should be appreciated that operation of the present invention is not limited to the particular blocks and/or the particular order of the blocks illustrated in FIGS. 2, 3 and 5. Accordingly, embodiments of the invention may provide functionality as described herein using various blocks in a sequence different than that of FIGS. 2, 3 and 5.

As part of the disclosure of the present invention, specific examples are included below. The examples are for illustrative purposes only and are not intended to limit the invention. Those of ordinary skill in the art will readily recognize parameters that can be changed or modified to yield essentially the same results.

EXAMPLE (Determination of Dehydrogenation Period, Regeneration Period and Total Slack Time)

The data in Table 1 are examples of typical programmable logic controller configurations that can be implemented in respective dehydrogenation processes for each listed hydrocarbon. Parameters including number of reactors, dehydrogenation time X, regeneration time Y, slack time Z, total cycle time, simultaneous on line (on stream) reactor(s) and hydrocarbon feed are listed in Table 1.

TABLE 1

Typical Data for Fixed Bed Dehydrogenation Unit without Modified Programmable Logic Controller

| Number of reactors | Symbol | 3 | 4 | 5 | 8 | 8 |
|---|---|---|---|---|---|---|
| Dehydrogenation time (min) | X | 9 | 9 | 9 | 14.3 | 9 |
| Regeneration time (min) | Y | 9 | 9 | 9 | 14.3 | 9 |
| Slack time (min) | Z | 6.11 | 4.5 | 4.5 | 7.15 | 4.5 |
| Total Cycle time (sec) | | 1444 | 1350 | 1350 | 2145 | 1350 |
| Simultaneous on stream reactor(s) | | 1.12 | 1.6 | 2 | 3.2 | 3.2 |
| Hydrocarbon | | Isobutane | Isobutane | Isobutane | Isopentane | Propane |

The data for the dehydrogenation unit that has five fixed bed reactors was used to construct a mathematical model for the dehydrogenation period X, regeneration period Y and total slack time Z. Days on stream (DOS) (also known as days on line) were 0 days and 1095 days (36 months). On day 0 (days on stream), the catalyst is able to absorb more endothermic heat, thus more heat can be delivered by the air in regeneration mode. Therefore, the ratio of X/Y is equal to 0.9. On day 1095 (days on stream), the activity of the catalyst declines, so less regeneration heat can be absorbed during the regeneration mode of the reactor. Thus, the ratio of X/Y increases to 1.2. The slack time (Z) and total cycle time (X+Y+Z) are kept constant throughout the whole process. The values for X/Y, X, Y, Z and total cycle time are listed in Table 2.

TABLE 2

Parameters for Modified Programmable Logic Controller

| Days on stream (DOS) | X/Y | Y (min) | X (min) | Z (min) | Total cycle (mins) |
|---|---|---|---|---|---|
| 0 | 0.9 | 9.47 | 8.53 | 4.5 | 22.5 |
| 1095 | 1.2 | 8.12 | 9.88 | 4.5 | 22.5 |

Figure 6:
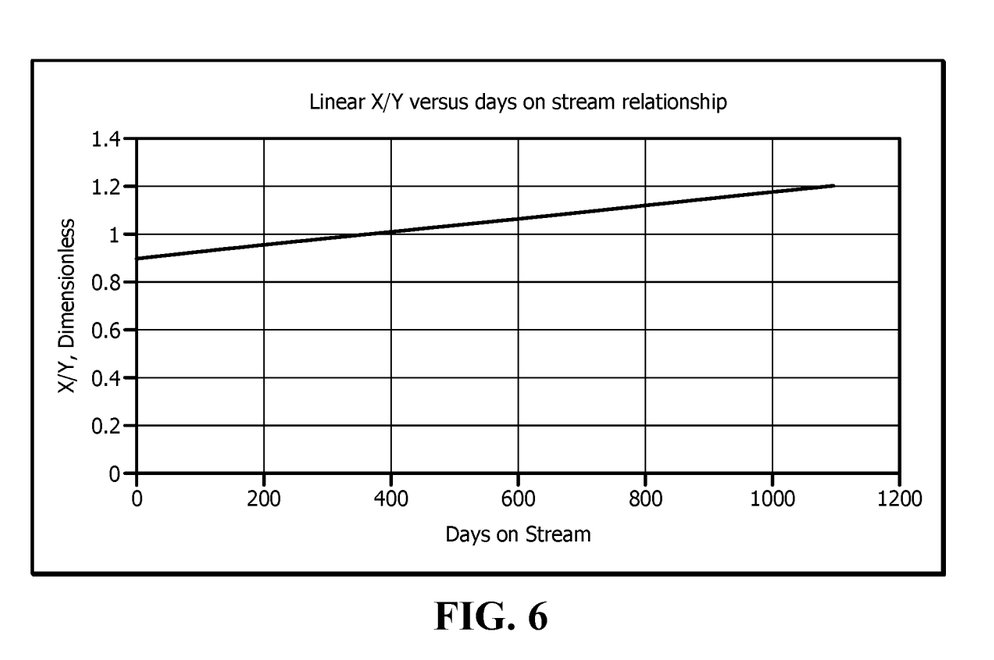
FIG. 6 shows a linear correlation between a ratio of period X to period Y and days on stream (on line), according to embodiments of the invention.

A linear regression between a ratio of X to Y and days on stream was performed based on the values in Table 2. As shown in FIG. 6, a linear correlation between X/Y and days on stream (DOS) was obtained as $(X/Y)=0.000289 \times DOS+0.9$. Subsequently, the correlation was written as $(18-Y)/Y=0.000289 \times DOS+0.9$, where X+Y was constant at 18 minutes over the cycles throughout the life expectancy L of the catalyst. The equation was further transformed by adding 1 on both sides thereof to $18/Y=0.000289 \times DOS+1.9$. Period Y was then derived as $Y=18/(0.000289 \times DOS+1.9)$, and X was derived as $X=18-Y$. The correlations can be further generalized as $Y=18/(1+\text{calculated } X/Y)$ and $X=18-18/(1+\text{calculated } X/Y)$, where X+Y was constant at 18 minutes. Since total cycle time X+Y+Z and slack time Z were constant, the overall sequencer program was still operable. Thus, the dehydrogenation period X and regeneration period Y can be manipulated by the modified programmable logic controller of the invention to optimize the utilization rate of the fixed bed reactors. The X/Y is a ratio of dehydrogenation time to catalyst regeneration time, which is a function of Arrhenius profile, or a function of a ratio of heat consumed by dehydrogenation to heat delivered by catalyst regeneration. Since X/Y here represents the ratio of heat consumed by dehydrogenation to heat delivered by catalyst regeneration, the correlation between X/Y and days on stream (DOS) is linear.

Operating at a correct ratio of X/Y for the dehydrogenation unit can minimize issues such as Houdry lump formation. In co-current operation of the fixed bed dehydrogenation unit, exact heat balance is difficult to reach. The hot spot in the fixed bed reactor constantly moves. When the hot spot moves inside of the catalyst bed towards the end of catalyst life, Houdry lump formation occurs. Varying Y based on the linear correlation described above can keep the hot spot at a theoretically calculated location that is out of the catalyst bed, thereby preventing the catalyst from overheating and forming lumps towards the end of the catalyst life. Furthermore, controlling dehydrogenation unit based on the linear correlation between X/Y and days on stream (DOS) can minimize the increase of the catalyst effectiveness factor between the start of run (SOR) and the end of run (EOR). Therefore, the control method is advantageous compared to the prior methods that keep a constant ratio of X to Y throughout the catalyst life.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of dehydrogenating a hydrocarbon, the method comprising:
   (1) flowing the hydrocarbon to a fixed bed reactor;
   (2) dehydrogenating the hydrocarbon in presence of a catalyst in the fixed bed reactor for period X, wherein the catalyst has life expectancy L;
   (3) regenerating, after period X, the catalyst for period Y, wherein $Z_1$ is a period between (2) and (3), if any,
   (4) repeating (2), after period Y, wherein $Z_2$ is a period between (3) and (4), if any, wherein $Z_1>0$ and/or $Z_2>0$ and $Z=Z_1+Z_2$, wherein a cycle of operating the fixed bed reactor is equal to X+Y+Z, wherein Z is total slack time which is defined as a total period of the cycle in which neither (2) nor (3) is being carried out; and
   (5) controlling the length of period X, the length of period Y, and the length of period Z, by a controller, such that Z<X/2 and Z<Y/2;
   wherein period X, period Y and total slack time Z in controlling step (5) are determined by a mathematical model based on one or more correlations obtained by linear regression or polynomial regression or multivariate multiple regression between (a) X, Y and/or Z and (b) one or more operating parameters and/or factors of the fixed bed reactor; and
   wherein the one or more operating parameters and/or factors of the fixed bed reactor are selected from the group consisting of days on stream, changes in process, number of fixed bed reactors in the dehydrogenation unit, catalyst conditions, and combinations thereof.

2. The method of claim 1, wherein the fixed bed reactor is disposed in a fixed bed dehydrogenation unit, the fixed bed dehydrogenation unit comprises one or more fixed bed reactors.

3. The method of claim 1, wherein the hydrocarbon is selected from the group consisting of on propane, isobutane, pentane, isopentane, n-butane, and combinations thereof.

4. The method of claim 1, wherein period X is in a range of 7 to 18 minutes, Y is in a range of 7 to 18 minutes, and Z is in arrange of 3.5 to 8.7 minutes.

5. The method of claim 1, wherein the changes in process comprise changing the hydrocarbon flowing to the fixed bed reactor, and wherein the hydrocarbon is one or more of propane, isobutane, pentane, isopentane, or n-butane.

6. The method of claim 1, wherein the catalyst conditions are selected from the group consisting of a reaction temperature, a reaction pressure, weight hourly space velocity, and combinations thereof.

7. The method of claim 6, wherein the weight hourly space velocity is in a range of 1 to 1.6.

8. The method of claim 1, wherein the one or more operating parameters and/or factors of the fixed bed reactor comprises days on stream.

9. The method of claim 6, wherein the reaction pressure is in a range of 0.2 bar to 1.2 bar.

10. The method of claim 1, wherein the correlations comprise a linear correlation between a ratio of X to Y and days on stream.

11. The method of claim 10, wherein a total length of period X and period Y is constant over cycles throughout life expectancy L.

12. The method of claim 10, wherein the linear correlation is determined by linear regression on operating data of the fixed bed dehydrogenation unit.

13. The method of claim 1, wherein the correlations comprise a polynomial correlation between (a) X, Y, Z and/or a ratio of X to Y and (b) the one or more operating parameters and/or factors of the fixed bed reactor, and wherein the polynomial correlation is obtained using polynomial regression based on operating data of the fixed bed dehydrogenation unit.

14. The method of claim 1, wherein the correlations between (a) X, Y and/or Z and (b) the one or more operating parameters and/or factors are obtained by multivariate multiple regression.

15. The method of claim 1, wherein the one or more operating parameters and/or factors of the fixed bed reactor comprises catalyst conditions.

16. The method of claim 1, wherein the one or more operating parameters and/or factors of the fixed bed reactor comprises the number of fixed bed reactors in the dehydrogenation unit.

17. The method of claim 1, wherein the one or more operating parameters and/or factors of the fixed bed reactor comprises changes in process.

18. The method of claim 1, wherein the changes in process comprise changing the hydrocarbon flowing to the fixed bed reactor, and wherein the hydrocarbon comprises at least one member selected from the group consisting of propane, isobutane, pentane and isopentane.

19. The method of claim 1, wherein the catalyst conditions are selected from the group consisting of a reaction pressure and a weight hourly space velocity.

* * * * *